United States Patent
Brüggemann et al.

(10) Patent No.: US 10,314,968 B2
(45) Date of Patent: *Jun. 11, 2019

(54) MEDICAL INJECTION DEVICE WITH ELECTRIC MOTOR DRIVE CONTROL

(71) Applicant: Sanofi-Aventis Deutschland GmbH, Frankfurt am Main (DE)

(72) Inventors: Ulrich Brüggemann, Frankfurt am Main (DE); Scott Preece, Coventry (GB); Christopher Langley, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 164 days.

This patent is subject to a terminal disclaimer.

(21) Appl. No.: 15/080,935

(22) Filed: Mar. 25, 2016

(65) Prior Publication Data

US 2016/0271323 A1    Sep. 22, 2016

Related U.S. Application Data

(63) Continuation of application No. 13/141,781, filed as application No. PCT/EP2009/067827 on Dec. 23, 2009, now Pat. No. 9,297,370.

(30) Foreign Application Priority Data

Dec. 27, 2008    (EP) .................................... 08022476

(51) Int. Cl.
*A61M 5/145*    (2006.01)
*A61M 5/142*    (2006.01)
(Continued)

(52) U.S. Cl.
CPC ...... *A61M 5/1452* (2013.01); *A61M 5/14244* (2013.01); *A61M 5/20* (2013.01);
(Continued)

(58) Field of Classification Search
CPC .. A61M 5/20; A61M 5/1452; A61M 5/14244; A61M 5/14566; A61M 2205/3306; A61M 2205/3365
(Continued)

(56) References Cited

U.S. PATENT DOCUMENTS

| | | |
|---|---|---|
| 533,575 A | 2/1895 | Wilkens |
| 3,701,345 A | 10/1972 | Heilman et al. |

(Continued)

FOREIGN PATENT DOCUMENTS

| | | |
|---|---|---|
| AU | 525126 | 10/1982 |
| EP | 0319267 A2 | 6/1989 |

(Continued)

OTHER PUBLICATIONS

Extended European Search Report issued in European Patent Application No. 17162265.7 dated Aug. 10, 2017.

*Primary Examiner* — Nathan R Price
*Assistant Examiner* — Anh Bui
(74) *Attorney, Agent, or Firm* — McCarter & English, LLP

(57) ABSTRACT

This invention relates to an injection device for delivering a medicament to the human or animal body, in particular, but not exclusively, to a device having a replaceable medicament cartridge, including an auto-injector, wherein the injector device comprises: a housing; a piston rod for driving a bung of a medicament container; a drive mechanism including a motor for providing an output drive to the piston rod for delivering the medicament; and control means for controlling operation of the device.

4 Claims, 6 Drawing Sheets

(51) Int. Cl.
*F04B 17/03* (2006.01)
*F04B 49/06* (2006.01)
*A61M 5/20* (2006.01)

(52) U.S. Cl.
CPC .............. *F04B 17/03* (2013.01); *F04B 49/06* (2013.01); *A61M 5/14566* (2013.01); *A61M 2205/3306* (2013.01); *A61M 2205/3365* (2013.01); *A61M 2205/502* (2013.01); *A61M 2205/8212* (2013.01)

(58) Field of Classification Search
USPC ............ 604/131, 151, 152, 154, 155, 890.1
See application file for complete search history.

(56) References Cited

U.S. PATENT DOCUMENTS

| | | |
|---|---|---|
| 4,908,017 A | 3/1990 | Howson et al. |
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,362,591 B1 * | 3/2002 | Moberg ............... A61M 5/162 318/685 |
| 6,899,698 B2 | 5/2005 | Sams |
| 6,936,032 B1 | 8/2005 | Bush, Jr. et al. |
| 7,241,278 B2 | 7/2007 | Moller |
| 9,297,370 B2 * | 3/2016 | Bruggemann .... A61M 5/14244 |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2009/0275916 A1 | 11/2009 | Harms et al. |

FOREIGN PATENT DOCUMENTS

| | | |
|---|---|---|
| EP | 0937471 A2 | 8/1999 |
| EP | 0937476 A2 | 8/1999 |
| GB | 2428745 A | 2/2007 |
| WO | 9938554 A1 | 8/1999 |
| WO | 0110484 A1 | 2/2001 |

\* cited by examiner

MEDICAL INJECTION DEVICE WITH ELECTRIC MOTOR DRIVE CONTROL

CROSS REFERENCE TO RELATED APPLICATIONS

The present application is a continuation of U.S. patent application Ser. No. 13/141,781 filed Oct. 22, 2011 which is a U.S. National Phase Application pursuant to 35 U.S.C. § 371 of International Application No. PCT/EP2009/067827 filed Dec. 23, 2009, which claims priority to European Patent Application No. 08022476.9 filed Dec. 27, 2008. The entire disclosure contents of these applications are herewith incorporated by reference into the present application.

This invention relates to injection devices for delivering medicine to the human or animal body and in particular, but not exclusively, to devices having a replaceable medicament cartridge, including auto-injectors. Such devices are commonly used by those with diabetes for the administration of insulin.

Medicament delivery devices are routinely used by persons without formal medical training, i.e. patients where self-management of their condition is increasingly common. These circumstances set a number of requirements for medicament delivery devices of this kind. The injector should be robust in construction, yet easy to use in terms of its operation by a user and the manipulation of the parts. In the case of those with diabetes, many users will be of impaired vision and may also be physically infirm. Devices that are too large of cumbersome may therefore prove difficult to use, particularly someone with reduced dexterity.

Patent Specification U.S. Pat. No. 6,340,357 describes a drug delivery system in which the dose setting is read into an electronic circuit and the dose setting movement of the dose setting elements relative to each other is performed by an electromechanical device, e.g. a motor controlled by the electronic circuit in accordance with the read in dose setting. The electronic control enables the apparatus to intervene by resetting a dose if a miss-handling of the device by the user is detected during dose setting, such as opening of the cartridge holder.

Patent Specification WO 2007/094833 describes a metering system for automatically adjusting for differential thermal expansion/contraction for the efficient, accurate and reproducible metered delivery of fluids. The system allows the metering system drive to re-zero itself to produce an accurate volumetric delivery of fluid from the dispensing container.

It is also known to detect a stall of the motor that drives the dose delivery and to warn the user if a dose fails to be delivered. However, there remains a problem in the resetting of the device following detection of a motor stall event.

It is an aim of the present invention to provide a medication delivery device that alleviates this problem.

According to the present invention, there is provided an injection device for delivering a medicament to a patient, wherein the injector device comprises: a housing; a piston rod for driving a bung of a medicament container; a drive mechanism including a motor for providing an output drive to the piston rod for delivering the medicament; and control means for controlling operation of the device; characterised in that:

the control means comprises: a drive signal generator for generating an input drive signal for the motor; an encoder for generating an encoder output signal indicative of the output drive of the motor; and means for varying the operational control of the device in dependence on a comparison between the input drive signal and the encoder output.

The input drive signal may be stepper pulses for driving the motor. The encoder output signal may be a pulsed signal having a timing characteristic that corresponds to the output drive of the motor. A plurality of reference points may be included in the device, each reference point being indicative of a different operational aspect of the device, including any one or more of: backstop position; dose delivered; door position; drive position; and reset threshold. The reference points preferably relate to the input drive signal such that respective reference points correspond to respective counts of the stepper pulses with reference to a device datum. A comparison between counts of the pulsed encoder output with counts of the stepper pulses may be indicative of motor slip. In the event that motor slip or stall is detected the control means is operative for determining the quantum of slip relative to one of the reference points whereupon said varying means adjusts the operational control of the device according to a predetermined criteria. The variation in operation control may be such as to urge the device to a target operational state. For example, when the quantum exceeds a predetermined threshold value, the motor may be deliberately stalled against a predetermined reference point representative of the target state. For example, the motor drive may be varied so the state of the device is changed to a dose reset position or a 'cartridge door open state' for enabling replacement of the cartridge. Alternatively, the motor may be controlled such as to rewind the piston rod to a backstop which defines a device datum or device reset position.

Embodiments of the present invention are advantageous in that the injector automatically initiates a reset action when necessary and without needing user interaction. This leads to an improvement in battery life and an avoidance or reduction in motor stall noise.

The invention will now be further described by way of example with reference to the accompanying drawings, in which like reference numerals designate like elements:

Figure 1:
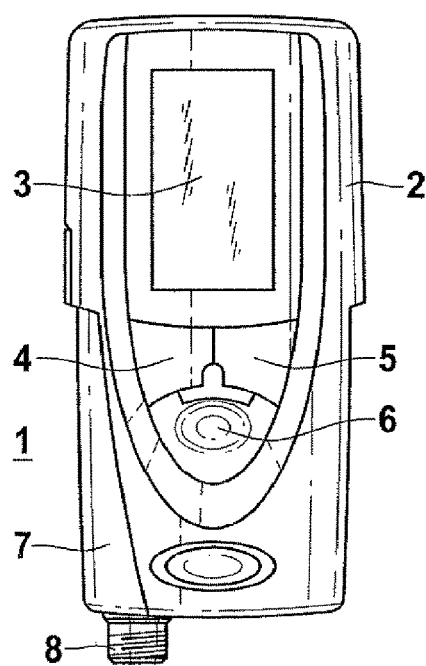
FIG. 1 is a front view of an auto-injector that may include an embodiment of the present invention.
Figure 2:
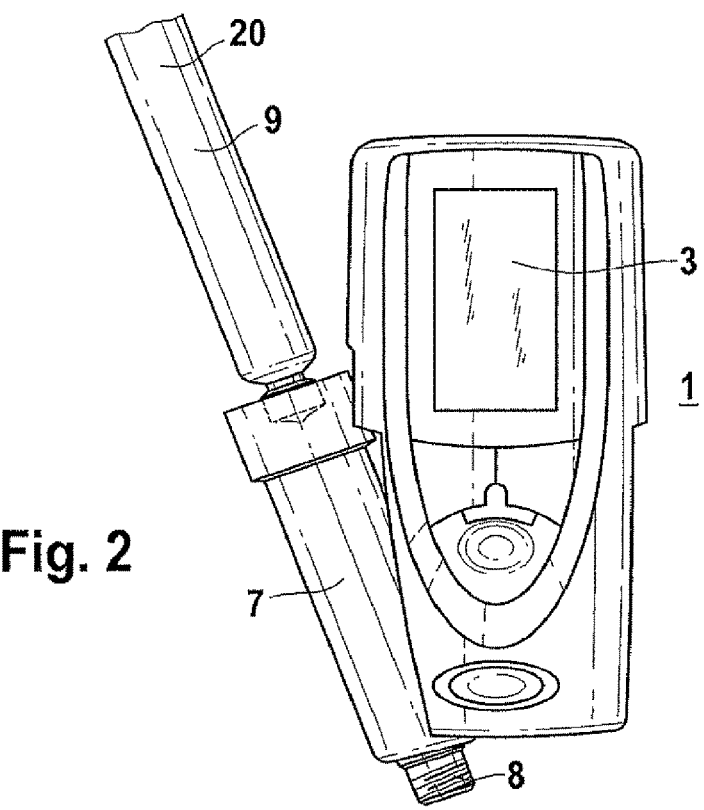
FIG. 2 is a front view of the auto-injector of FIG. 1 with a medicament cartridge door shown in an open position for receiving a medicament cartridge.

In FIG. 1, an auto-injector 1 comprises a case 2 having a display 3 for displaying functional information relating to the operation of the auto-injector, including the set dose, number of doses remaining in the medicament cartridge. User interface buttons 4, 5 and 6 are provided to allow the user to operate the injector including priming, setting a dose, opening a medicament cartridge holder and door 7, and activating the dispensing of the set dose. A threaded needle attachment 8 is provided to which a needle can be attached for dose delivery and subsequently removed and discarded. A cover (not shown) may be provided to fit over the lower portion of the case 2 to assist in protect the device from the ingress of particles and fluid. FIG. 2 shows the auto-injector 1 with the cartridge holder and door 7 in an open position for receiving a replacement medicament cartridge 9.

Figure 3:
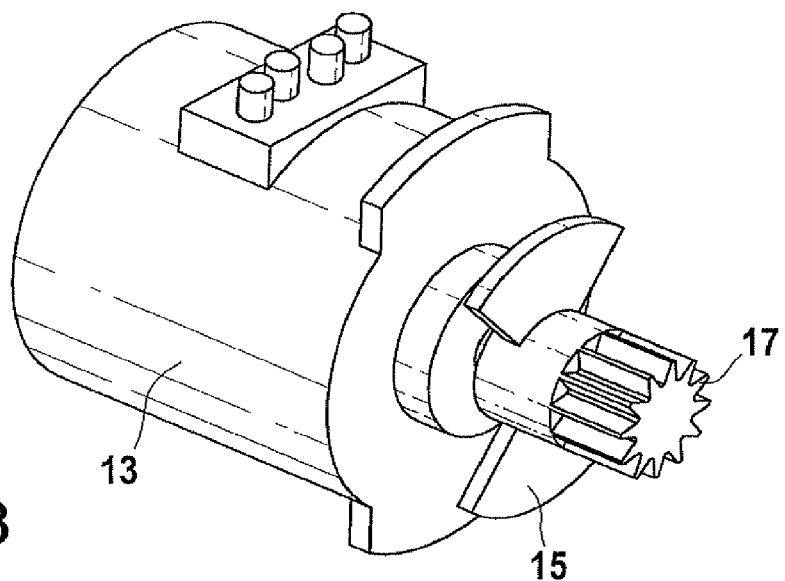
FIG. 3 is a perspective view of a motor for use in embodiments of the present invention.
Figure 6:
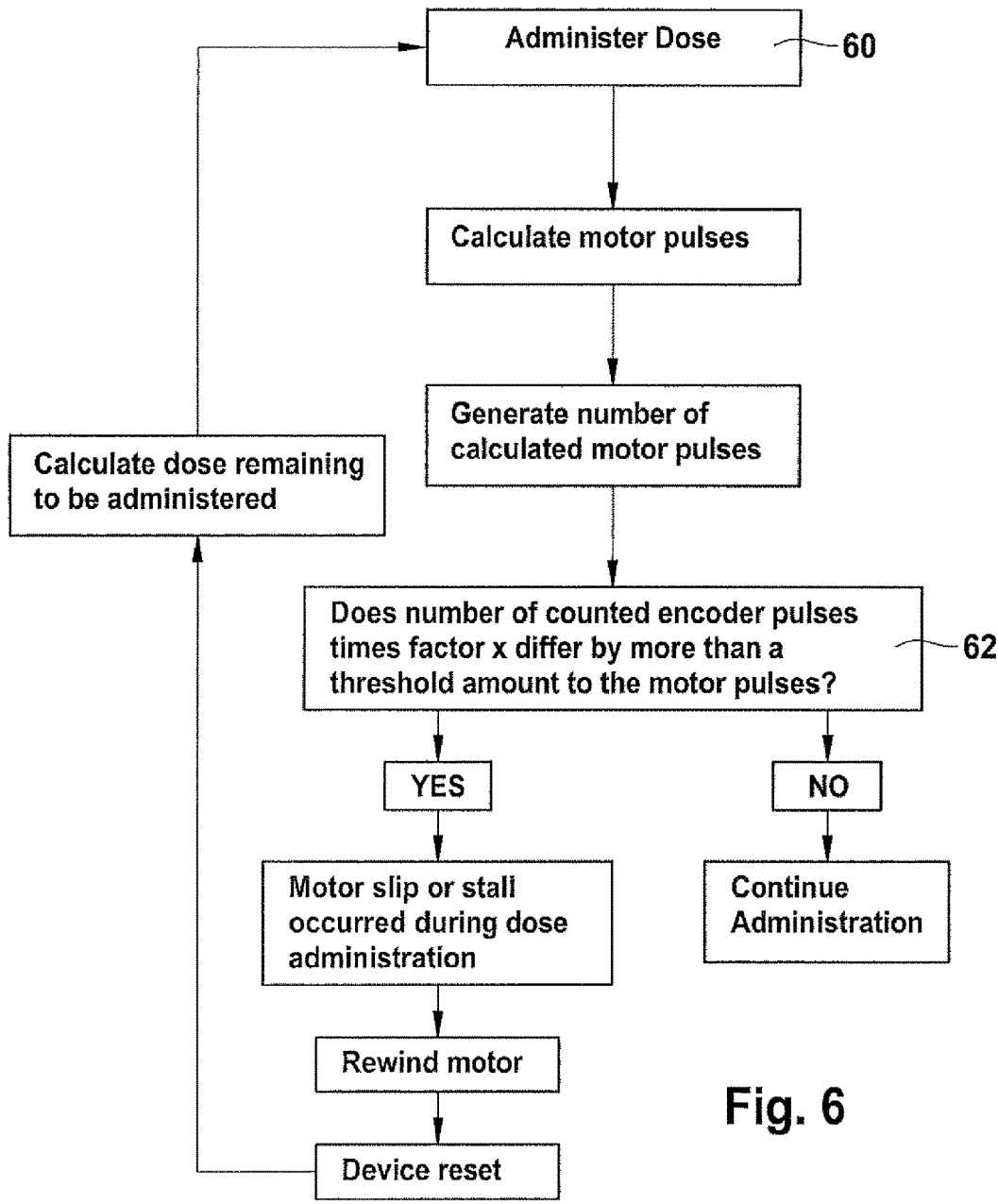
FIG. 6 is a flow chart illustrating a decision sequence that may be performed by the control means.
Figure 7:
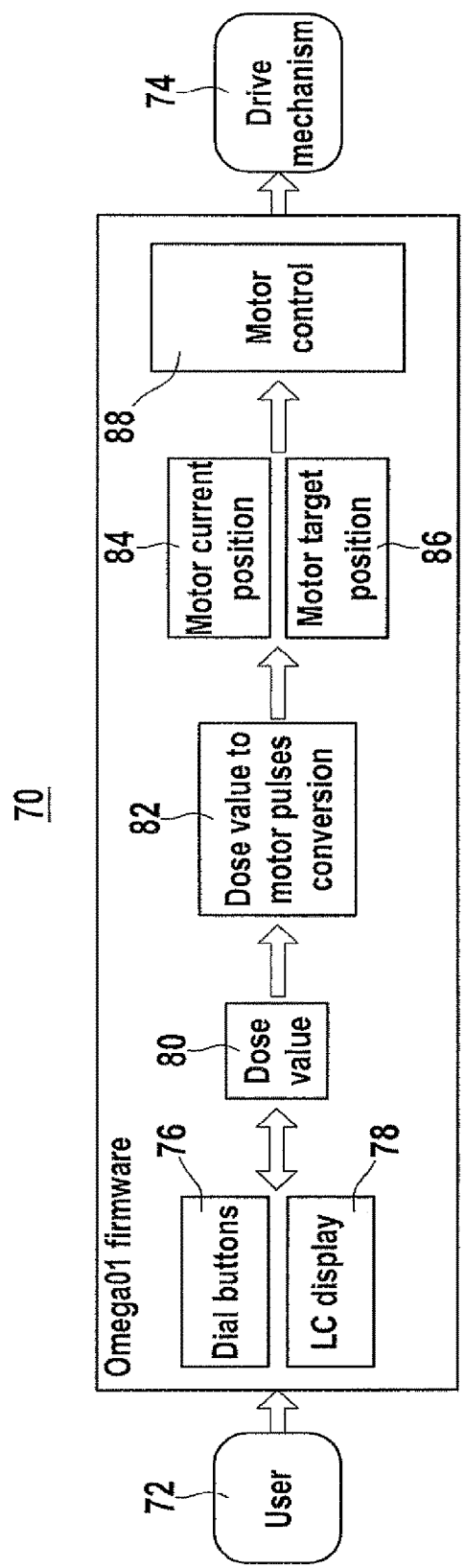
FIG. 7 is a functional block diagram of the control means.

FIG. 3 shows a motor 13 within a drive mechanism (see FIG. 7). The motor is provided with a pair of flags 15 disposed at 180 degrees with reference to one another. An output gear 17 engages with a gear train (not shown) of the drive mechanism for driving the piston rod of the auto-injector 1. The motor 13 may be a stepping motor driven by a pulsed drive signal or stepper pulses illustrated schematically in FIGS. 5a and 5b below. The pulsed drive signal is generated by an electronic control circuit within the control means. The control means will be described in more detail with reference to FIGS. 5a to 7.

Figure 4:
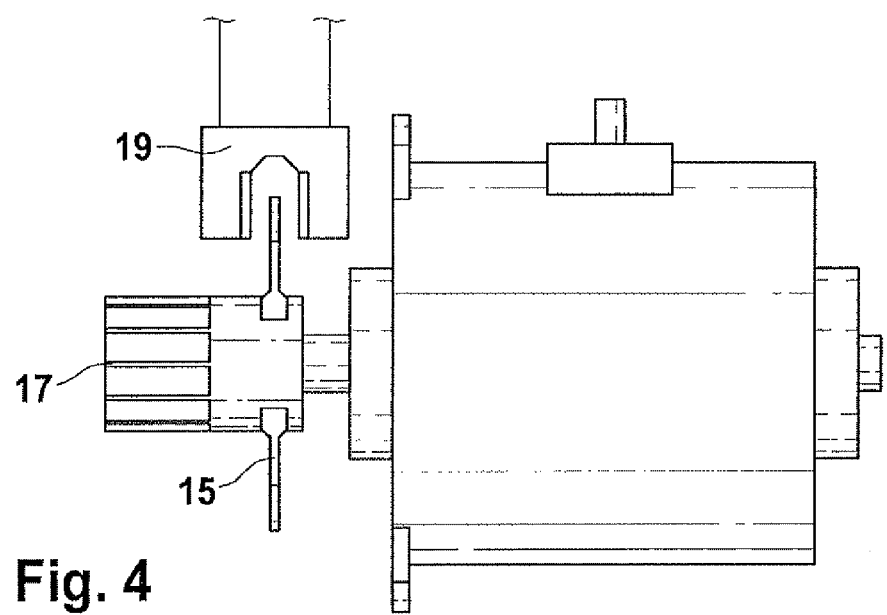
FIG. 4 is a side view of the motor of FIG. 3 with an encoder.

FIG. 4 is a side view of the motor 13 showing an optical encoder 19 in registration with the flags 15. As the drive shaft of the motor 13 rotates the flags 15, every edge of a flag causes a change in the output of the optical encoder 19, so that the encoder outputs a series of output pulses representative of the angular velocity of the drive shaft. The control means (microcontroller/microprocessor—not shown) detects and counts these pulses. The encoder signal causes an interrupt in the microcontroller/microprocessor. An interrupt causes an interruption of the current software program flow, executes a special interrupt software routine and returns to the normal software flow after finishing the interrupt routine. This technique is used to react immediately to external signals to make sure that every signal is recognized by the microprocessor. In the embodiment shown in FIG. 4, a pair of flags 15 is located at 180° and will therefore generate 4 pulses per motor turn. One encoder pulse is therefore equivalent to 5 motor pulses, assuming 20 motor pulses for a single turn of the motor shaft.

Figure 5A:
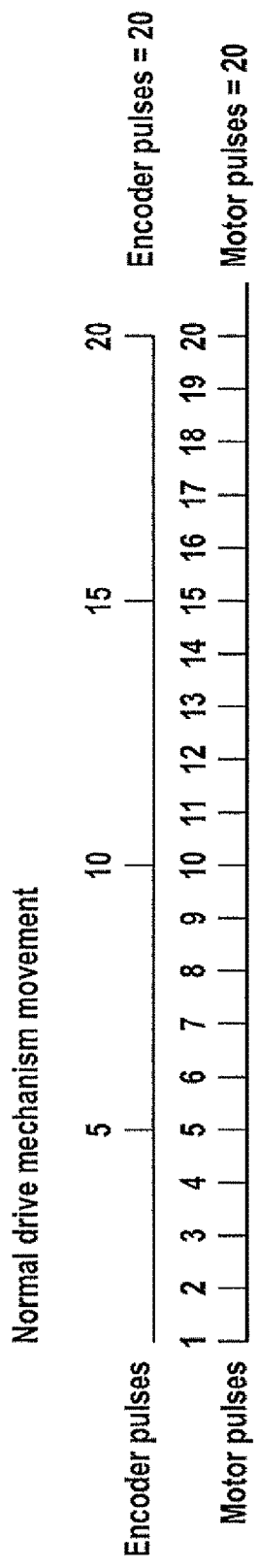
FIG. 5a is a timing chart of motor drive and encoder output.
Figure 5B:
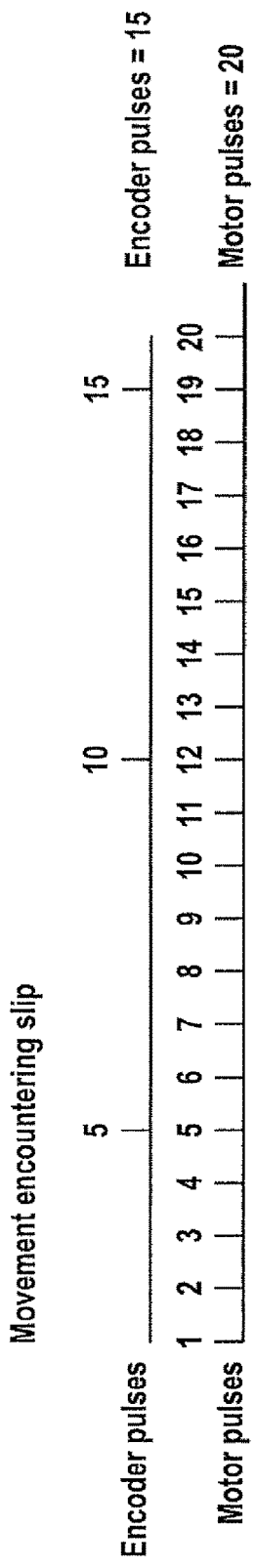
FIG. 5b is a timing chart of motor drive and encoder output showing motor slip.

FIG. 5a illustrates the relative timing between the motor drive or stepper pulses and the encoder output pulses during normal drive mechanism movement of the device. In this example, there are 5 motor stepper pulses to one encoder output pulse, the control means being programmed to expect 5 motor stepper pulses to one encoder output pulse. Consequently, when 20 motor stepper pulses are counted at the same time that the control means counts 4 encoder output pulses, the control comparison determines that the device is driving normally. That is, there is no motor slippage or no motor stall. FIG. 5a illustrates a situation where a count comparison between the encoder pulse output is such as to indicate 15 motor stepper pulses whereas the actual count by the control means corresponds to 19 or 20 pulses. In this case the control means determines from the comparison that the motor movement has encountered slippage. At this point, a subroutine is run by software programmed into the control means to make a determination as to the state of the auto-injector in relation to predetermined reference points and a device datum position. The position of the piston rod when in a fully retracted position may represent a backstop position or datum position (i.e. "zero") from which other device reference points may be referenced. The datum position also corresponds to an absolute motor position so that incremental movements relative to that correspond to other operational states of the device. These other device reference points are between zero and a maximum motor travel position through 26858 motor stepper pulses. For example, from the datum position, a medicament cartridge 9 door latch open position may be represented by, for example, a motor position that corresponds to "datum position+4 pulses". A priming dose may be determined to have been effected by movement of the motor 13 through 84 pulses from the backstop datum position.

FIG. 6 shows an example of an administration routine that may be run with the control means software during the administration of medicament. At 60, the user inputs via input buttons 4-6 a desire to start the administration of a dose of medicament. The motor stepper and encoder pulse counts are examined at step 62 to determine if they differ from one another by more than a predetermined amount. If YES, the control means rewinds the drive mechanism until the motor stalls at the backstop, at which point the device may be datumed or reset. The control means software may then calculate the deficit in the medicament administered and perform means to administer this dose. If NO, the administration continues until the dose is completely expelled.

FIG. 7 is a functional block diagram of the control means 70, to which is connected a user input 72 corresponding to the user interface buttons 4-6 of FIG. 1, and the drive mechanism 74. The control means 70 includes dial buttons 76 through which the user can dial the required dose and an LC display 78 for displaying the set dose. The control means software sets a dose value corresponding to that set by the user at 80 and converts this into an appropriate pulse value for the stepper motor 13 at 82. At 84, the software determines the current position of the motor 13 by looking at the current pulse count of the stepper pulses generated by the motor and determines a motor target position 86 in terms of stepper pulses that corresponds to the reference point representative of the piston rod position that will deliver the dose set at 76/80. The control means software, motor control 88, generates the required stepper pulses to drive the motor 13 of the drive mechanism 74 and compares encoder and motor pulses.

The invention claimed is:

1. A controller for controlling operation of an injection device for delivering a medicament, the controller comprising:
   a drive signal generator that generates an input drive signal for driving a motor, the input drive signal for driving the motor comprising stepper pulses; and
   an encoder that generates an encoder output signal indicative of an output drive of the motor the encoder output signal being a pulsed signal having a timing characteristic that corresponds to the output drive of the motor,
   wherein the controller varies the operational control of the device based, at least in part, on a comparison between the input drive signal and the encoder output signal,
   wherein a comparison between counts of the encoder output signal with counts of the stepper pulses of the input drive signal provides an indication of a quantum of motor slip,
   wherein the motor is deliberately stalled against a predetermined reference point when the quantum of slip exceeds a predetermined threshold value, and
   wherein the controller calculates a deficit in the medicament administered that is a dose remaining to be administered and performs administration of the dose remaining to be administered.

2. A controller according to claim 1, further comprising user interface buttons.

3. A controller according to claim 1, further comprising dose dial buttons.

4. A method of delivering a medicament to a patient using an injection device comprising a housing; a piston rod for driving a bung of a replaceable medicament container, the piston rod retractable to a backstop position; a drive mechanism including a motor for providing an output drive to the piston rod for delivering a user settable dose of the medicament and retracting the piston rod to the backstop position; and a controller that controls operation of the injection device, the controller including a drive signal generator that generates an input drive signal for driving the motor and an encoder that generates an encoder output signal indicative of the output drive of the motor, wherein the input drive signal for driving the motor comprises stepper pulses, wherein the encoder output signal is a pulsed signal having a timing characteristic that corresponds to the output drive of the motor, wherein the method comprises:

starting administration of a dose of the medicament to a patient;

determining, by the controller, a number of motor pulses and a number of encoder pulses;

varying the operational control of the device based, at least in part, on a comparison between the input drive signal and the encoder output signal including determining, by the controller, if counts of stepper pulses of the input drive signal and counts of encoder pulses differ from one another by more than a predetermined amount, wherein a comparison between counts of the encoder output signal with the counts of the stepper pulses of the input drive signal provides an indication of a quantum of motor slip;

stalling, by the controller, the motor against a predetermined reference point when the quantum of slip exceeds a predetermined threshold value;

calculating, by the controller, a deficit in the medicament administered that is a dose of medicament remaining to be administered; and performing administration of the dose of medicament remaining to be administered.

\* \* \* \* \*

UNITED STATES PATENT AND TRADEMARK OFFICE
CERTIFICATE OF CORRECTION

PATENT NO. : 10,314,968 B2
APPLICATION NO. : 15/080935
DATED : June 11, 2019
INVENTOR(S) : Bruggemann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this
Thirty-first Day of December, 2019

Andrei Iancu
*Director of the United States Patent and Trademark Office*